(12) United States Patent
McCullough

(10) Patent No.: US 11,571,511 B2
(45) Date of Patent: Feb. 7, 2023

(54) INSERTION MECHANISM AND METHOD OF INSERTING A NEEDLE OF A DRUG DELIVERY DEVICE

(71) Applicant: AMGEN INC., Thousand Oaks, CA (US)

(72) Inventor: Adam B. McCullough, Westlake Village, CA (US)

(73) Assignee: AMGEN INC., Thousand Oaks, CA (US)

( * ) Notice: Subject to any disclaimer, the term of this patent is extended or adjusted under 35 U.S.C. 154(b) by 197 days.

(21) Appl. No.: 16/488,466

(22) PCT Filed: Feb. 20, 2018

(86) PCT No.: PCT/US2018/018687
§ 371 (c)(1),
(2) Date: Aug. 23, 2019

(87) PCT Pub. No.: WO2018/164829
PCT Pub. Date: Sep. 13, 2018

(65) Prior Publication Data
US 2020/0238004 A1 Jul. 30, 2020

Related U.S. Application Data

(60) Provisional application No. 62/468,190, filed on Mar. 7, 2017.

(51) Int. Cl.
*A61M 5/158* (2006.01)
*A61M 5/142* (2006.01)

(52) U.S. Cl.
CPC ........ *A61M 5/158* (2013.01); *A61M 5/14248* (2013.01); *A61M 2005/14256* (2013.01); *A61M 2005/1585* (2013.01)

(58) Field of Classification Search
CPC .............. A61M 5/158; A61M 5/14248; A61M 2005/1585; A61M 2005/14256;
(Continued)

(56) References Cited

U.S. PATENT DOCUMENTS 6,800,070 B2 * 10/2004 Mazidji ............... A61M 5/3234
604/179
2004/0092874 A1 5/2004 Mazidji et al.
(Continued)

FOREIGN PATENT DOCUMENTS

CN 1870961 A 11/2006
JP 2010525869 A 7/2010
(Continued)

OTHER PUBLICATIONS

Singapore Patent Application No. 11201908058U, Search Report and Written Opinion, dated Nov. 30, 2020.
(Continued)

*Primary Examiner* — Kevin C Sirmons
*Assistant Examiner* — Avery Smale
(74) *Attorney, Agent, or Firm* — Marshall, Gerstein & Borun LLP

(57) ABSTRACT

An insertion mechanism for a drug delivery device. The insertion mechanism includes a proximal end, a distal end, a first opening disposed near the proximal end, and a second opening disposed in the distal end. A needle or cannula assembly is disposed within a housing and has a base with a proximal surface and a distal surface and a needle or cannula coupled to the distal surface. A retraction member is disposed within the housing to maintain the needle or cannula assembly in a retracted position before movement to an extended position, the retraction member in contact with the base. Upon supplying pressure through the first opening until an amount of pressure P1 applies an application force
(Continued)

to the proximal surface of the base that surpasses a resistive force of the retraction member, the needle or cannula assembly is moved from the retracted position to the extended position.

19 Claims, 4 Drawing Sheets

(58) Field of Classification Search
CPC ........... A61M 2005/1583; A61M 2005/14252; A61M 2005/1426; A61M 2205/8218; A61M 2205/8281; A61M 5/14244; A61M 5/145; A61M 2005/1587
See application file for complete search history.

(56) References Cited

U.S. PATENT DOCUMENTS

| | | |
|---|---|---|
| 2004/0116847 A1 | 6/2004 | Wall |
| 2007/0016159 A1 | 1/2007 | Sparholt et al. |
| 2007/0088268 A1 | 4/2007 | Edwards |
| 2008/0269687 A1 | 10/2008 | Chong et al. |
| 2009/0069750 A1* | 3/2009 | Schraga ............ A61M 5/14248 604/167.02 |
| 2010/0152674 A1 | 6/2010 | Kavazov et al. |
| 2014/0094769 A1* | 4/2014 | Hwang ............ A61M 5/14248 604/506 |

FOREIGN PATENT DOCUMENTS

| | | |
|---|---|---|
| WO | WO-2009033032 A1 | 3/2009 |
| WO | WO-2011116304 A1 | 9/2011 |
| WO | WO-2015055747 A1 | 4/2015 |
| WO | WO-2015164647 A1 * | 10/2015 ............ A61M 5/158 |

OTHER PUBLICATIONS

International Search Report for International Application No. PCT/US2018/018687, dated May 30, 2018.
Written Opinion for International Application No. PCT/US2018/018687, dated May 30, 2018.
Japanese Patent Application No. 2019-548732, Notice of Rejection, dated Nov. 9, 2021.
Singapore Patent Application No. 11201908058U, Written Opinion, dated Aug. 19, 2022.

* cited by examiner

INSERTION MECHANISM AND METHOD OF INSERTING A NEEDLE OF A DRUG DELIVERY DEVICE

CROSS-REFERENCE TO RELATED APPLICATION

This is the United States National Phase of PCT/US18/18687, filed Feb. 20, 2018, which claims the priority benefit of U.S. Provisional Patent Application No. 62/468,190, filed Mar. 7, 2017, the entire contents of each of which are hereby incorporated herein by reference.

FIELD OF THE DISCLOSURE

The present disclosure generally relates to drug delivery devices and, more particularly, mechanisms and methods for inserting or deploying a needle and/or cannula of a drug delivery device.

BACKGROUND

Some drug delivery devices, such as on-body injectors, may be temporarily attached to a patient to deliver a drug via an injection needle or some other means over an extended period of time. The drug delivery device may be attached to the tissue of the patient's abdomen, thigh, arm, or some other portion of the patient's body.

In some cases, the drug delivery device may be worn by the patient for several minutes or hours while the drug is injected. For example, viscous drugs, including some biologics, can have long injection times due to the force needed to expel them from the drug delivery device. Furthermore, some drug delivery devices are configured to be attached to the patient at a doctor's office, and then later deliver the drug to the patient when the patient returns to his or her home. For these reasons and others, a rigid injection member may be left inside the patient for a substantial amount of time, which can result in patient discomfort or unease.

In addition, some existing drug delivery devices use external features for needle safety, requiring the patient to remove the drug delivery device while a rigid needle is still inside the patient. Depending upon the angle, depth, and stiffness of the needle, this can cause patient discomfort and the anxiety of seeing the needle afterward.

As a result, insertion mechanisms have been disposed within drug delivery devices to accomplish insertion and/or retraction movements of the needle. Such an insertion mechanism, however, may increase the overall size, complexity, and/or cost of the drug delivery device.

SUMMARY

In accordance with a first aspect, a wearable drug delivery device comprises a main housing having a container, a fluid pathway connector coupled to the container, and a pressure supply device. The drug delivery device further comprises an insertion mechanism disposed within the main housing and operatively coupled to the pressure supply device, the fluid pathway connector defining a fluid flow path between the container and the insertion mechanism. The insertion mechanism includes a housing having a proximal end, a distal end, a first opening disposed near the proximal end, and a second opening disposed in the distal end, the first opening coupled to the pressure supply device. A needle or cannula assembly is disposed within the housing and moveable between a retracted position and an extended position. The needle or cannula assembly includes a base having a proximal surface and a distal surface, and a needle or cannula coupled to the distal surface of the base. The base divides the housing into a proximal chamber and a distal chamber. A retraction member is disposed within the housing to maintain the needle or cannula assembly in the retracted position before movement to the extended position. The retraction member is in contact with the base and applies a resistive force. The pressure supply device supplies pressure through the first opening and into the proximal chamber until an amount of pressure P1 in the proximal chamber applies an application force to the proximal surface of the base that surpasses the resistive force of the retraction member to move the needle assembly from the retracted position to the extended position. The needle is disposed through the opening in the distal end of the housing in the extended position to deploy the needle.

In accordance with a second aspect, an insertion mechanism for a drug delivery device comprises a housing having a proximal end, a distal end, a first opening disposed near the proximal end of the housing, the first opening adapted to be operatively coupled to a pressure supply device, and a second opening disposed in the distal end of the housing. A needle or cannula assembly is disposed within the housing and moveable between a retracted position and an extended position. The needle or cannula assembly includes a base having a proximal surface and a distal surface, and a needle or cannula is attached to the base. A retraction member is contact with the base and applies a resistive force to maintain the needle or cannula assembly in the retracted position before movement to the extended position. Pressure is supplied through the first opening until an amount of pressure P1 applies an application force to the proximal surface of the base that exceeds the resistive force of the retraction member to move the needle or cannula assembly from the retracted position to the extended position, the needle extending through the second opening in the distal end of the housing in the extended position.

In accordance with yet another aspect, a method of deploying a needle of an insertion mechanism from a drug delivery device is disclosed. The method comprises maintaining a retracted position of a needle or cannula assembly disposed within a housing of the insertion mechanism by a retraction member. The method also comprises supplying pressure to a first opening of the housing of the insertion mechanism until an amount of pressure P1 in a proximal chamber of the housing imparts an application force on a base of the needle or cannula assembly that exceeds a resistive force applied to the base by one or more of the retraction member or a pressure P2 in a distal chamber of the housing. The method also comprises moving the needle assembly from the retracted position to the extended position upon the application force surpassing the resistive force. The method still further comprises disposing a needle of the needle or cannula assembly through a second opening in a distal end of the housing of the insertion mechanism upon movement of the needle assembly to the extended position to deploy the needle.

In further accordance with any one or more of the foregoing first and second aspects and method, the insertion mechanism for a drug delivery device and method may include any one or more of the following forms or method steps.

In one form, the retraction member may include a biasing mechanism, and the biasing mechanism including a spring having a first end attached to the base and a second end attached to the distal end of the housing, wherein the spring retracts the needle into the retracted position after release of pressure P1 in the proximal chamber. In addition, the insertion mechanism may further comprise a first connector upwardly extending from the proximal surface of the base, and a flexible fluid path member having a first end operatively coupled to the connector upwardly extending from the proximal surface of the base and a second end operatively coupled to a second connector downwardly extending from the proximal end of the housing. The flexible fluid path member is moveable with the needle assembly. In addition, the flexible fluid path member may be in an extended position when the needle assembly is in the extended position and a compressed position when the needle assembly is in the retracted position.

In another form, the insertion mechanism may further include a step disposed around the housing sidewall near the distal end of the housing. The step may have a sealing mechanism, and the sealing mechanism may include an o-ring. Further, the distal surface of the base may contact the o-ring to soften the impact when the needle or cannula assembly moves from the retracted position to the extended position. In addition, the housing may include a sidewall having a threaded inside surface, and the base may further include one or more of a surface or a pair of side surfaces in contact with the inside surfaces of the sidewall. The side surfaces of the base may each have a threaded surface corresponding to the threaded inside surface of the sidewall of the housing. In addition, the threaded inside surface of the sidewall of the housing and the threaded surface of the side surfaces of the base may include one of coarse threading or fine threading, the coarse threading allowing the needle to rotate at least two to three times during insertion, and the fine threading allowing the needle to rotate at least eight to ten times during insertion.

In yet another form, the base may include a surface or a pair of side surfaces minimally spaced from the sidewall of the housing to minimize flow-around when pressure is supplied to the proximal chamber. Also, the retraction member may comprise a frictional element in contact with a sidewall of the base. The frictional element may comprise one or more of at least one sealing mechanism or o-ring. In addition, upon one of applying negative pressure through the first opening or supplying positive pressure to a third opening disposed in a sidewall of the housing near the distal end of the housing, a pressure P2 in the distal chamber may surpass the pressure P1 in the proximal chamber causing the needle or cannula assembly to move back upward into the retracted position after needle deployment.

In yet another form, the needle or cannula assembly may be secured back into the retracted position by one or more of: (1) at least one spring-loaded directional latch, or (2) at least one groove disposed on the sidewall of the housing. The at least one groove for receiving the at least one sealing mechanism may be disposed on the sidewall of the base to prevent the needle assembly from being activated again into the extended position. In addition, the at least one spring-loaded directional latch may include a first spring-loaded directional latch disposed on one area of the sidewall of the housing and a second spring-loaded latch disposed on another area of the sidewall of the housing. Each latch may have an angled side surface that contacts a corresponding angled side surface of the base on either side of the base to secure the base of the needle or cannula assembly, preventing redeployment. Further, the at least one groove may include a first groove disposed on one area of the sidewall of the housing and a second groove disposed on another area of the sidewall of the housing. Each groove may be adapted to receive a corresponding frictional element disposed on the sidewall of the base to secure the base of the needle or cannula assembly, preventing redeployment.

Still further, in other forms, when the pressure P1 in the proximal chamber exceeds a pressure P2 in the distal chamber, and the needle or cannula assembly may move from the retracted position to the extended position.

In one form of the method, maintaining a retracted position of a needle or cannula assembly may comprise one of: (1) applying a resistive force to a distal surface of a base of the needle assembly via a biasing mechanism, or (2) disposing a frictional element on at least one area of a sidewall of the base and applying the resistive force toward the proximal end of the housing via the frictional element.

In another form of the method, the method may further comprise one of supplying negative pressure through the first opening or positive pressure to a third opening disposed in the housing near the distal end of the housing until a pressure P2 in a distal chamber of the housing exceeds the pressure P1 in the proximal chamber, causing the needle or cannula assembly to move from the extended position back to the retracted position. In addition, the method may further comprise securing the needle assembly in the retracted position after movement from the extended position to prevent redeployment of the needle of the needle assembly. In some examples, securing the needle assembly in the retracted position may comprise one of: (1) providing at least one spring-loaded directional latch on a sidewall of the housing that contacts at least one side of the base upon movement into the at least one spring-loaded directional latch, or (2) inserting at least one sealing mechanism disposed on at least one side of the base into a corresponding groove disposed on the sidewall of the housing. In addition, the method may further include increasing a size of the proximal chamber as the needle or cannula assembly moves from the retracted position to the extended position and reducing an output force present at a time of needle deployment.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the example embodiments, except as may be explicitly delineated in the corresponding written description. Also, none of the drawings is necessarily to scale.

DETAILED DESCRIPTION

A wearable drug delivery device having a new insertion mechanism is disclosed. The insertion mechanism is disposed within a main housing of the drug delivery device and includes a housing having a proximal end, a distal end, a sidewall, a first opening disposed near the proximal end, and a second opening disposed in the distal end of the housing. Generally, the first opening receives pressure from a pressure supply device to deploy a needle through the second opening in the housing.

More specifically, the insertion mechanism further includes a needle or cannula assembly disposed within the housing and moveable between a retracted position and an extended position. The needle or cannula assembly includes a base having a proximal surface and a distal surface and a needle coupled to the distal surface, the base dividing the housing into a proximal chamber and a distal chamber. A retraction member maintains the needle in the retracted position before movement to the extended position to deploy the needle. Pressure is applied through the first opening of the housing and into the proximal chamber until an amount of pressure P1 in the proximal chamber applies an application force to the proximal surface of the base that exceeds a resistive force of the retraction member to move the needle or cannula assembly from the retracted position to the extended position. In the extended position, the needle is disposed through the second opening of the housing to deploy the needle. To withdraw the needle and move the needle or cannula assembly from the extended position back into the retracted position, one of negative pressure is supplied to the proximal chamber or positive pressure is applied to the distal chamber until the pressure P2 in the distal chamber is greater than the pressure P1 in the proximal chamber, for example. When the pressure P2 exceeds the pressure P1, the needle assembly is retracted and secured back into the retracted position to prevent reuse.

Figure 1:
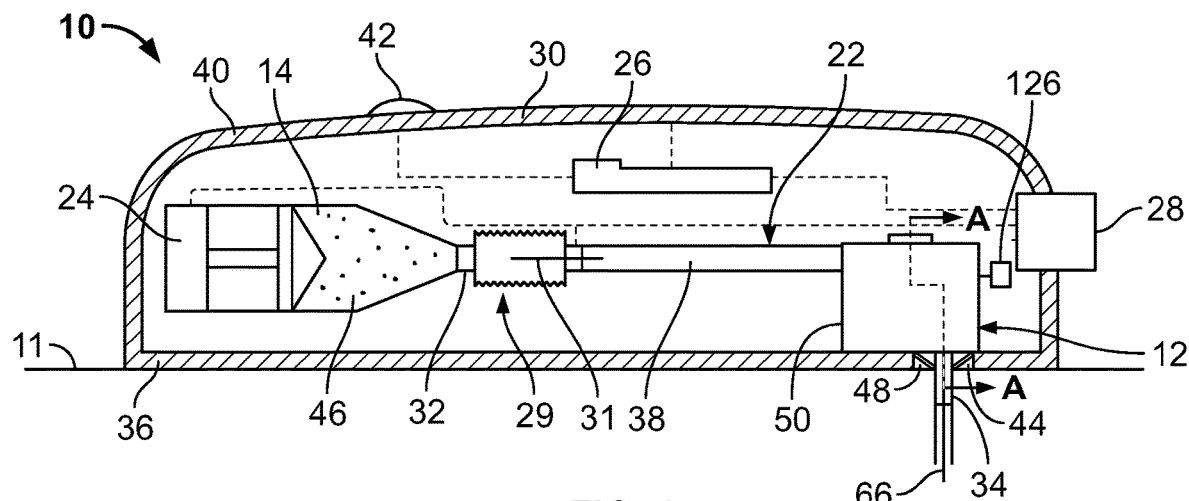
FIG. 1 is a schematic representation of one embodiment of a drug delivery device having an insertion mechanism in accordance with teachings of the present disclosure.

More specifically, and referring now to FIG. 1, a wearable drug delivery device 10 having an insertion mechanism 12 according to the present disclosure is depicted. In at least one example, the drug delivery device 10 may be configured as a wearable drug delivery device, such as an on-body injector, that may be attached to a patient's tissue 11 (e.g., the patient's skin) to administer delivery of a drug treatment. The drug delivery device 10 may automatically deliver a subcutaneous injection of a fixed or a patient/operator-settable dose of a drug over a controlled or selected period of time. The drug delivery device 10 may be intended for self-administration by the patient, but may also be used by a caregiver or a formally trained healthcare provider to administer an injection.

The drug delivery device 10 may include a container 14 coupled to the insertion mechanism 12 by a fluid pathway connector 22, a drive mechanism 24, and a controller 26, each of which may be disposed in a main housing 30 of the drug delivery device 10. An actuator 28 (e.g., a depressible button) may be arranged on an exterior of the main housing 30 and configured to initiate operation of the drug delivery device 10 by activating the insertion mechanism 12, the drive mechanism 24, and/or the controller 26 via mechanical and/or electrical means (shown in dotted lines in FIG. 1). The fluid pathway connector 22 defines a sterile fluid flow path 38 between the container 14 and the insertion mechanism 12. The fluid pathway connector 22 may include a container access mechanism 29 configured to insert a container needle 31 through a septum 32 associated with the container 14 to establish fluid communication between the container 14 and the sterile fluid flow path 38 in response to activation of the drug delivery device 10, for example, via the actuator 28. The main housing 30 may include a bottom wall 36 to be releasably attached (e.g., adhered with an adhesive) to the patient's skin 11, and a top wall 40 including one or more indicator lights 42 and/or a window (not illustrated) for viewing the container 14. An opening 44 may be formed in the bottom wall 36, and optionally a septum 48 may extend across the opening 44 to seal the interior of the main housing 30 prior to use. The exterior of the insertion mechanism 12 may be defined by an insertion mechanism housing separate from the main housing 30, as explained more below relative to each example insertion mechanism.

Generally, upon activation of the drug delivery device 10, the insertion mechanism 12 may insert a needle or cannula 34 of a needle or cannula assembly and/or a trocar 66 through the opening 44 and/or septum 48 and into the patient. Simultaneously or subsequently, the drug delivery device 10 may enable, connect, or open necessary connections to establish fluid communication between the container 14 and the fluid pathway connector 22. Next, the drive mechanism 24 may force a drug 46 stored in the container 14 through the sterile fluid flow path 38 of the fluid pathway connector 22 and into the cannula 34 for subcutaneous delivery to the patient.

Figure 2:
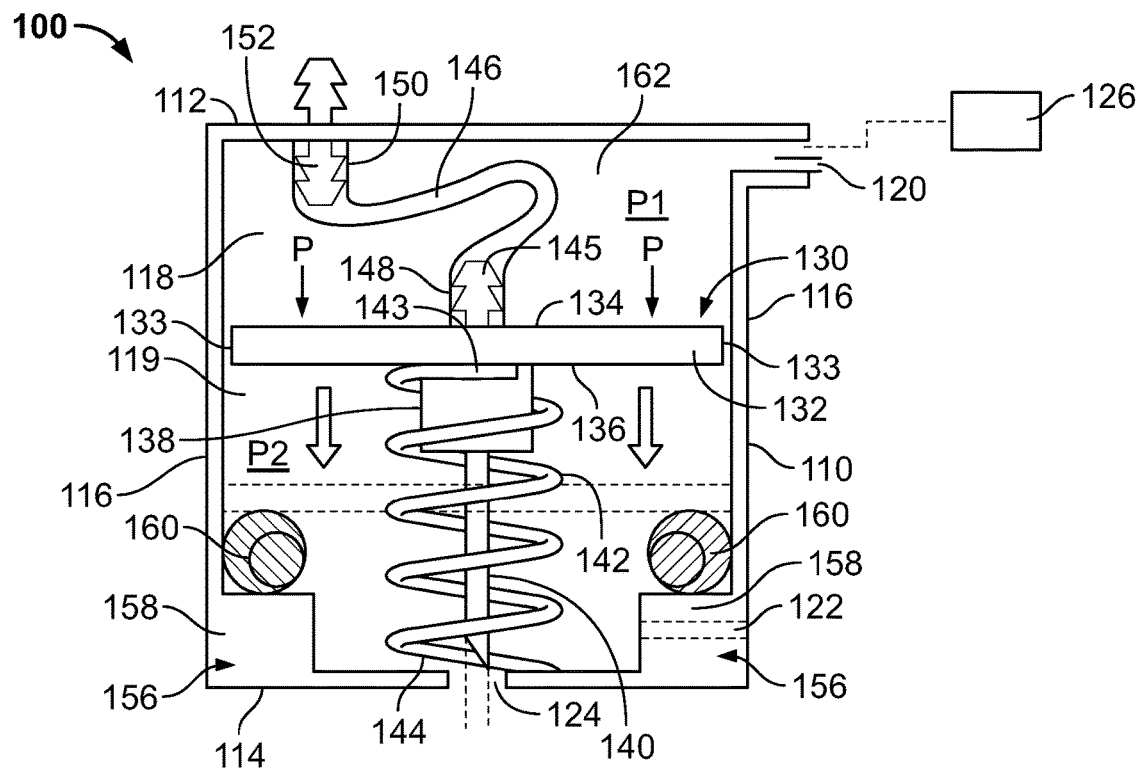
FIG. 2 is a cross-sectional view of an insertion mechanism according to one aspect of the present disclosure taken along the line A-A of the FIG. 1, the insertion mechanism in a retracted position.
Figure 3:
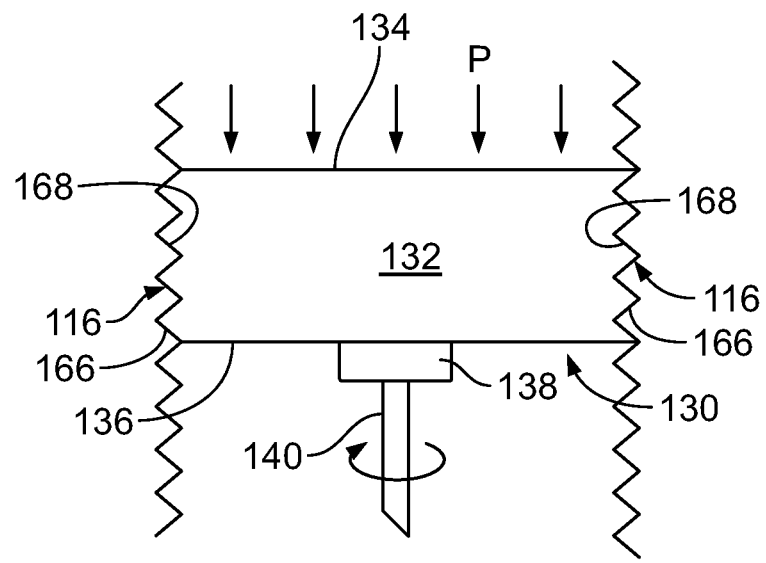
FIG. 3 is a cross-sectional view of portions of the insertion mechanism of FIG. 2, the insertion mechanism having a base and a housing according to another aspect of the present disclosure.
Figure 4:
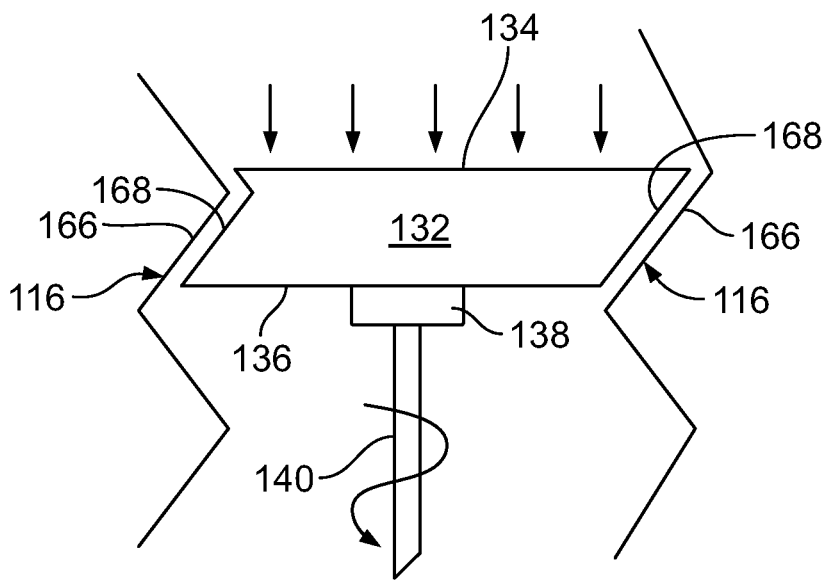
FIG. 4 is another cross-sectional view of portions of the insertion mechanism of FIG. 2, the insertion mechanism having another base and another housing according to yet another aspect of the present disclosure.

FIGS. 2-4 illustrate an insertion mechanism 100 corresponding to one example of the insertion mechanism 12 illustrated in FIG. 1. The insertion mechanism 100 may be incorporated in a drug delivery device such as the drug delivery device 10 depicted in FIG. 1. The insertion mechanism 100 includes a housing 110 having a proximal end 112, a distal end 114 disposed opposite the proximal end 112, a sidewall 116 disposed between the proximal and distal ends 112, 114, a first opening 120 disposed near the proximal end 112, and a second opening 124 disposed on the distal end 114. The first opening 120 is adapted to be coupled to a pressure supply device 126. The pressure supply device 126 may supply pressurized fluid or gas and may include any pressure source, such as a pneumatic pressure source and any other source for providing pressure, as one of ordinary skill in the art will understand. In addition, the pressure supply device 126 is disposed within the main housing 30 of the drug delivery device 10 of FIG. 1, and may be directly or indirectly coupled to the first opening 120 of the insertion mechanism 100.

As further depicted in FIG. 2, a needle or cannula assembly 130 is disposed within the housing 110 of the insertion mechanism 100 and is moveable between a retracted position, as depicted in FIG. 2, and an extended position. The extended position is depicted in dashed lines in FIG. 2, as further explained below. The needle or cannula assembly 130 includes a base 132 having a proximal surface 134 and a distal surface 136. The proximal surface 134 is disposed closer to the proximal end 112 of the housing 110. Likewise, the distal surface 136 is disposed closer to the distal end 114 of the housing 110. In addition, a hub 138 extends downwardly from the distal surface 136 the base 132, and a needle or cannula 140 is attached to the base 132 via the hub 138, in this example. More specifically, and in one example, the needle or cannula 140 is attached to and downwardly extends from the hub 138 and is adapted to extend into and out of the second opening 124 disposed on the distal end 114 of the housing 110 in the extended position. Although not depicted in this example, the needle or cannula 140 may alternatively be directly attached to the base 132 and still fall within the scope of the present disclosure. The base 132 and the hub 138 may be circular or cylindrical in shape. Alternatively, each of the base 132 and the hub 138 may take the form of various other shapes and configurations and still fall within the scope of the present disclosure.

As further depicted in FIG. 2, the base 132 of the needle or cannula assembly 130 divides the housing 110 into a proximal chamber 118 and a distal chamber 119. In one example, the proximal chamber 118 has a pressure P1, and the distal chamber 119 has a pressure P2. Each of the pressures P1 and P2 in the respective proximal and distal chambers 118, 119 can vary, which can determine whether the needle or cannula assembly 130 is in the retracted position or the extended position, as explained more below.

In another example, and as depicted in FIG. 2, the base 132 may include one or more of a side surface or a pair of side surfaces 133 that is minimally spaced from the sidewall 116 of the housing 110 to minimize flow-around when pressure is supplied to the proximal chamber 118, for example, along with the thickness of the base 132. Said another way, the tight clearance between the sidewalls 116 of the housing 110 and the side surfaces 133 of the base 132 minimize flow-around when the proximal chamber 118 is pressurized.

A retraction member 142 is also disposed within the housing 110. The retraction member 142 is in contact with the base 132 and applies a resistive force that maintains the needle or cannula assembly 130 in the retracted position before movement to the extended position, as described more below. More specifically, in this example, the retraction member 142 applies the resistive force, such as a biasing force, to the distal surface 136 of the base and includes a first end 143 attached to the distal surface 136 of the base 132 and a second end 144 in contact with the distal end 114 of the housing 110. The retraction member 142 downwardly extends from the distal surface 136 of the base 132 around the needle 140 and to the distal end 114 of the housing 110. More specifically, and in one example, the retraction member 142 is a biasing mechanism, such as a compression spring, and is biased in the retracted position depicted in FIG. 2. Upon release of pressure P1 in the proximal chamber 118, the biasing mechanism, e.g., spring, retracts the needle or cannula 140 back into the retraction position, for example.

In another example, the retraction member 142 may alternatively be an extension spring having a first end attached to the proximal surface 134 of the base 132 and a second end attached to the proximal end 112 of the housing 110. Having the extension spring as the retraction member 142 would accomplish the same purpose as having the compression spring as the retraction member 142 described above. For example, the extension spring would also bias the needle or cannula assembly 130 in the retracted position of FIG. 2 and, therefore, retract the needle or cannula 140 back into the retracted position when pressure P1 is released from the proximal chamber 118.

In another example, the insertion mechanism 100 further includes a first connector 145 upwardly extending from the proximal surface 134 of the base 132, and a second connector 152 downwardly extending from the proximal end 112 of the housing 110 into the proximal chamber 118. A flexible fluid path member 146 includes a first end 148 operatively coupled to the first connector 145, and a second end 150 operatively connected to the second connector 152. So configured, the flexible fluid path member 146 extends and retracts with the needle or cannula assembly 130. Said another way, the flexible fluid path member 146 also moves from the retracted position to the extended position, consistent with when the needle assembly 130 moves from the retracted position to the extended position. In other words, the flexible fluid member 146 moves with the needle assembly from the retracted position, in which the flexible fluid path member 146 is in a compressed position, and the extended position, in which the flexible fluid path member 146 is in an extended position.

In another example, the flexible fluid path member 146 may alternatively and/or additionally be used as a retraction member. More specifically, the flexible fluid path member 146 may serve as the biasing mechanism that biases the needle or cannula assembly 130 in the retracted position of FIG. 2. So configured, when pressure P1 increases in the proximal chamber 118, the flexible fluid path member 146 stretches or expands to an extended position. Likewise, when the pressure P1 decreases, the flexible fluid path member 146 moves back to the retracted position of FIG. 2 to retract the needle 140 after deployment. In this example, the flexible fluid path member 146 includes a line having a material with appropriate elasticity to achieve this functionality.

In another example, the insertion mechanism 100 may include a third connector 153 upwardly extending from the proximal end 112 of the housing 110 outside of the housing 110. An external fluid path member 155 includes a first end 157 operatively coupled to the third connector 153, and a second end 159 operatively coupled to the fluid pathway connector (FIG. 1). So configured, and in one example, the drug may be expelled through the fluid pathway connector 22, through the external fluid path member 155, through the flexible fluid path member 146, through the needle or cannula 140 and into the patient. While the external fluid path member 155 is depicted as a curved, L-shaped member, the external fluid path member 155 may alternatively include various other forms and shapes and still fall within the scope of the present disclosure. For example, the external fluid path member 155 may be any other connecting member that operatively couples the flexible fluid path member 146 to the fluid pathway connector 22 (FIG. 1).

The insertion mechanism 100 further includes a step 156 disposed on and/or around the sidewall 116 of the housing 11 near the distal end 114 of the housing 110. The step 156 includes a sealing mechanism 160, such as an o-ring or any other sealing mechanism known to persons of ordinary skill in the art that can achieve the same function. The distal surface 136 of the base 132 contacts the sealing mechanism 160 to soften the impact of the distal surface 136 of the base 132 against the shoulders 160 when the needle or cannula assembly 130 is moved to the extended position. In addition, the sealing mechanisms 160, e.g., o-rings, prevent leakage and hold the pressure once the needle or cannula 140 is inserted into the patient's skin, for example, softening the impact.

In operation, needle assembly 130 is biased in the retracted position by the resistive force of the retraction member 142 to prevent migration of the needle 140 or needle assembly 130 during shipping, storage or any other handling. To deploy the needle 140, the pressure supply device 126, for example, supplies pressure through the first opening 120 into the proximal chamber 118. The needle or cannula assembly 130 remains stationary via the retraction member 142 while the pressure increases in the proximal chamber 118. When the pressure P1 in the proximal chamber applies an application force to the proximal surface 134 that exceeds the resistive force of the retraction member 142, the needle or cannula assembly 130 begins to move out of the retracted position and into the extended position. In another example, when the pressure P1 in the proximal chamber 118 exceeds or surpasses the pressure P2 in the distal chamber 119, the needle or cannula assembly 130 moves from the retracted position to the extended position. In the extended position, the distal surface 136 of the base 132 contacts the sealing mechanisms 160 disposed on the shoulders 158 near the distal end 114 of the housing 110 and the needle 140 is extended through in the second opening 124 and into the patient's skin with sufficient force. When the needle assembly 130 and, thus, the base 132 moves toward the distal end 114 of the housing 110, the proximal chamber 118 becomes larger, such that the output force of the needle 140 will decrease. In other words, because an initial build-up of pressure P1 is allowed in the proximal chamber P1 while the needle assembly 130 is in the retracted position, there is a reduction in output force that naturally occurs as the proximal chamber P1 volume increases.

Thus, as is understood by persons having ordinary skill in the art, the insertion force of the needle 140 and speed can be controlled in the insertion mechanism 100 by adjusting the pressure supplied to the proximal chamber 118, the flow rate of the pressure being supplied, and the area of the base 132 of the needle or cannula assembly 130. In addition, a slight over-penetration, resulting from a bounce in the sealing mechanisms 160 disposed on the step 158 upon contact with the distal surface 136 of the base 132, may reduce the incidence of tissue blocking the needle or cannula 140 during needle deployment. In addition, only a light force is needed to retract the needle or cannula 140 back into the housing 110 of the insertion mechanism 100, minimizing the retraction member 142, such as the spring, requirements. If pressure supplied fails, the needle 140 will retract back into the retracted position.

Referring now to FIGS. 3 and 4, the insertion mechanism 100 of FIG. 2 may alternatively include a sidewall 116 that is threaded. More specifically, the housing 110 of the insertion mechanism 100 may include a sidewall 116 having a threaded inside surface 166. In a similar manner, instead of being minimally spaced from the sidewall 116, the base 132 of the needle or cannula assembly 130 may alternatively include side surfaces 168 in contact with the threaded inside surfaces 166 of the sidewall 116 of the housing 110. More specifically, each side surface 168 of the base 132 may also be threaded, such as having a threaded surface that corresponds exactly to the threaded inside surface 166 of the sidewall 116. In one example, and as depicted in FIG. 3, the threaded inside surfaces 166 of the sidewall 116 and the threaded side surfaces 168 of the base 132 include fine threading. In this example, the fine threading allows the needle or cannula 140 to rotate at least eight to ten times during deployment, for example. As one of ordinary skill in the art will appreciate, the needle or cannula 140 may alternatively rotate more than eight to ten times during deployment and still fall within the scope of the present disclosure. In another example, and as depicted in FIG. 4., the threaded inside surfaces 166 of the sidewall or sidewalls 116 and the threaded side surfaces 168 of the base 132 include coarse threading. This larger pitch thread allows the needle 140 to rotate fewer times during deployment. In one example, the coarse threading allows the needle or cannula 140 to rotate two to three times during deployment.

So configured, this threaded interface between the sidewall 116 of the housing 110 and the side surfaces 168 of the base 132 enables a controlled rotation of the needle or cannula 140 during entry of the needle or cannula 140. As further depicted in FIG. 4, the corresponding threaded portions may be loosely fit together, e.g., there is a small space between the threaded sidewall 166 of the housing 110 and the threaded side surfaces 168 of the base 132 to reduce friction and create a smoother rotation during needle deployment. Moreover, in both examples of FIGS. 3 and 4, the rotation during needle deployment helps reduce axial deflection of the needle or cannula 140, enabling a more comfortable and effective needle deployment.

Figure 5:
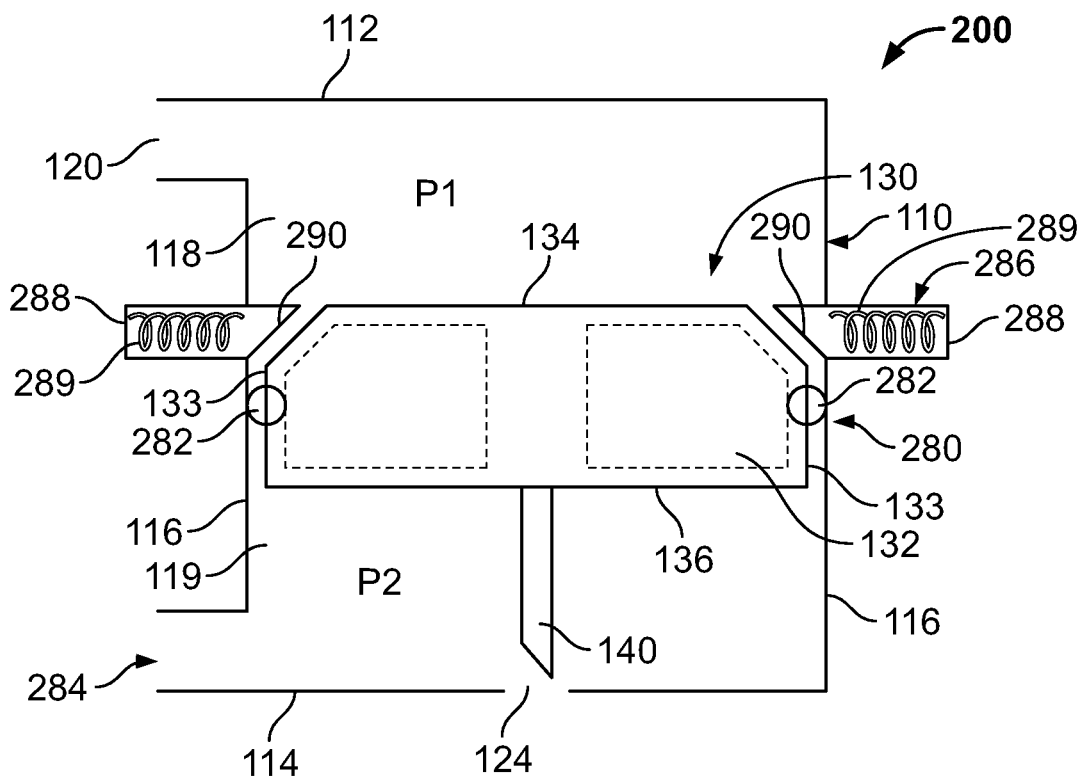
FIG. 5 is a cross-sectional view of another insertion mechanism according to another aspect of the present disclosure taken along the lines A-A of FIG. 1, the insertion mechanism in a retracted position.

Referring now to FIG. 5, another exemplary insertion mechanism 200 according to the present disclosure is depicted. More specifically, and as explained more below, the retraction member of the insertion mechanism 200 is not a spring 142, as depicted in FIG. 2, for example, but instead includes at least one frictional element 280. The at least one frictional element 280 applies a resistive force to maintain the needle or cannula assembly 130 in the retracted position, as explained more below, and is in contact with a sidewall 133 of the base 132. More generally, the insertion mechanism 200 is identical to the insertion mechanism 100 depicted in FIG. 2 and explained above, except for the additional and/or alternative structural features included in FIG. 5 and explained below. For the sake of brevity, parts of the insertion mechanism 200 identical to the insertion mechanism 100 share the same reference numerals and are explained relative to the insertion mechanism 100 only.

More specifically, the at least one frictional element 280 of the insertion mechanism 200 includes a pair of sealing mechanisms 282 disposed in the sidewall 133 of the base 132. The at least one frictional element 280, such as the sealing mechanisms 282, applies the resistive force toward the proximal end 112 of the housing 110. In this example, each sealing mechanism 282 is disposed in an approximate mid-point of the sidewall of the base 133. Alternatively, the sealing mechanisms 282 may be disposed on any other portion of the sidewall 133 of the base 132 and still fall within the scope of the present disclosure. In one example, the sealing mechanisms 282 are o-rings. Any other similar type of seal may alternatively be used and also still fall within the scope of the present disclosure. Similar to the retraction member 142 of the insertion mechanism 100, the at least one frictional element 280, e.g., the sealing mechanisms 282, prevent migration of the needle or cannula 140 of the needle assembly 130 during one or more of shipping, storage or any other handling of the insertion mechanism 200.

In operation, pressure is supplied to the first opening 120 of the housing 110 of the insertion mechanism 200 to deploy the needle or cannula 140 of the needle or cannula assembly 130. More specifically, when the pressure P1 in the proximal chamber 118 applies an application force to the proximal surface 134 of the base 132 that exceeds or surpasses the resistive force of the at least one frictional member 280, the needle or cannula assembly 130 is moved from retracted position to the extended position. In another example, when the application force of the pressure P1 on the proximal surface 134 of the base exceeds the resistive force of the pressure P2 in the distal chamber 119, the application force of the pressure P1 overcomes the force of the at least one frictional element 280, e.g., the sealing mechanisms 282, to move the needle or cannula assembly 130 from the retracted position to the extended position and effect needle deployment.

In this example, the housing 110 of the insertion mechanism 200 further includes a third opening 284. The third opening 284 is disposed near the distal end 114 of the housing 110, such as in the sidewall 116, and opens into the distal chamber 119. Alternatively, the third opening 284 may be disposed on any other portion of the housing 110 such that the third opening 282 opens into or is in communication with the distal chamber 119 of the housing 110. After the needle or cannula assembly 130 is moved to the extended position, and in some cases after the pressure P1 in the proximal chamber 118 is vented, pressure is supplied to the third opening 284 and into the distal chamber 119. When the pressure P2 in the distal chamber 119 exceeds the pressure P1 in the proximal chamber 118, the needle 140 is retracted back into the housing 110 through the opening 124 and the needle assembly 130 is moved back into the retracted position. In this example, a small pressure as tactile feedback is provided to the patient just after the needle 140 is withdrawn and pressure continues to be applied or supplied to the distal chamber 119 via the third opening 284.

Alternatively, a negative pressure may be applied to the proximal chamber 118 through the first opening 120 to decrease the pressure P1 in the proximal chamber 118. When the pressure P1 in the proximal chamber 118 is less than the pressure P2 in the distal chamber 119, the needle 140 moves back to the retracted position from the extended position. Said another way, and regardless of whether positive pressure is applied through the third opening 284 or negative pressure is applied through the first opening 120, when the pressure P2 exceeds the pressure P1 after deployment of the needle 140, the needle 140 and needle assembly 130 are moved back to the retracted position from the extended position.

After the needle or cannula assembly 130 is moved back into the retracted position, the insertion mechanism 200 secures the needle or cannula assembly 130 in the retracted position to prevent reuse of the needle 140, for example. More specifically, and as depicted in FIG. 5, the insertion mechanism 200 further includes at least one latch 286 for securing or maintaining the needle or cannula assembly 140 back in the retracted position. In one example, the at least one latch 286 includes a pair of spring-loaded directional latches 288. A first spring loaded directional latch 288 is disposed on one area of the sidewall 116 of the housing, and a second spring-loaded directional latch 288 is disposed on another area of the sidewall 116 of the housing, such that the first and second spring-loaded latches are disposed at the same height and position on the corresponding areas of the sidewall 116 of the housing 110. In addition, each of the first and second spring-loaded latches has a spring 289 and an angled surface 290 facing an interior of the housing 110. Each spring 289 is disposed around each latch 288 to bias each latch 288 in a direction toward the base 134 of the needle or cannula assembly 130. In this example, the base 134 further includes an angled corner or surface 292 on each side 133. The angled surface 292 on each sidewall 133 of the base 132 contacts the corresponding angled surfaces 290 of the latches 288 after movement of the needle or cannula assembly 130 into the retracted position. The biasing force of each spring-loaded latch 288 in the direction toward the base 134 secures the base 134 and, therefore, the needle or cannula assembly 140 in the retracted position to prevent redeployment.

Figure 6:
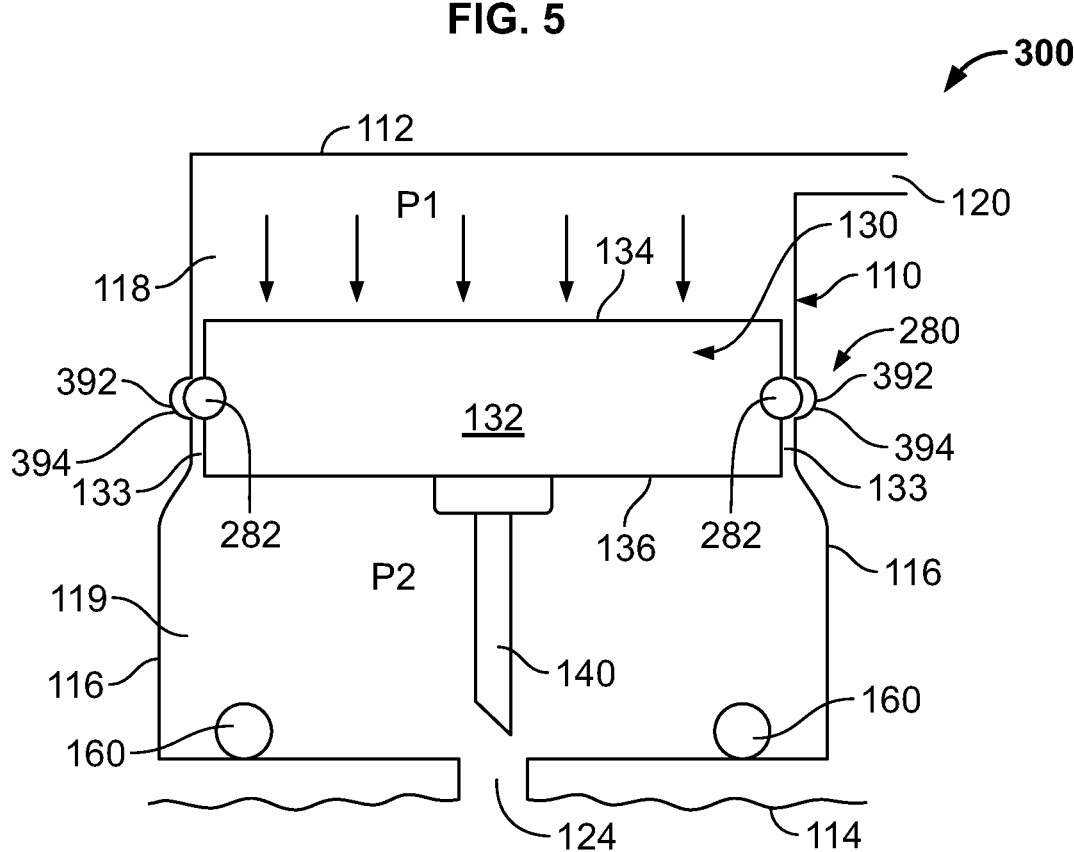
FIG. 6 is a cross-sectional view of another insertion mechanism according to yet another aspect of the present disclosure taken along the lines A-A of FIG. 1, the insertion mechanism in a retracted position.

Referring now to FIG. 6, another exemplary insertion mechanism 300 according to the present disclosure is depicted. More specifically, and like the insertion mechanism 200 of FIG. 5, the retraction member of the insertion mechanism 300 is not a spring 142, as depicted in FIG. 2, for example, but instead includes at least one frictional element 280 in contact with the base 132. The at least one frictional element 280 applies a resistive force to maintain the needle or cannula assembly 130 in the retracted position, as explained more below. In addition, the insertion mechanism 300 also includes a different manner of locking the needle or cannula assembly 130 back into the retracted position to prevent reuse that is unlike both insertion mechanism 100 and 200. More generally, the insertion mechanism 300 is identical to the insertion mechanisms 100 and 200 depicted in FIGS. 2 and 5, respectively, and explained above, except for the additional and/or alternative structural features included in FIG. 6 and explained below. For the sake of brevity, parts of the insertion mechanism 300 identical to the insertion mechanism 100 share the same reference numerals and are explained relative to the insertion mechanism 100 only.

More specifically, and like the insertion mechanism 200 of FIG. 5, the at least one frictional element 280 of the insertion mechanism 300 includes a pair of sealing mechanisms 282 disposed in the sidewall 133 of the base 132. The at least one frictional element 280, such as the sealing mechanisms 282, applies a resistive force toward the proximal end 112 of the housing 110. In this example, each sealing mechanism 282 is again disposed in an approximate mid-point of the sidewall of the base 133. Alternatively, the sealing mechanisms 282 may be disposed on any other portion of the sidewall 133 of the base 132 and still fall within the scope of the present disclosure. In one example, the sealing mechanisms 282 are o-rings. Any other similar type of seal may alternatively be used and also still fall within the scope of the present disclosure. Similar to the retraction member 142 of the insertion mechanism 100, the at least one frictional element 280, e.g., the sealing mechanisms 282, prevents migration of the needle or cannula 140 of the needle assembly 130 during one or more of shipping, storage or any other handling of the insertion mechanism 200.

In addition to the sealing mechanisms 282, the insertion mechanism 300 may further includes at least one groove 392 to help maintain the needle or cannula assembly 130 in the retracted position before needle insertion. In one example, the at least one groove 392 includes a pair of grooves 394. A first groove 394 is disposed on one area of the sidewall 116 of the housing, and a second groove 394 is disposed on another area of the sidewall 116 of the housing, such that the first and second grooves 394 are disposed at the same height and position on the corresponding areas of the sidewall 116 of the housing 110. In addition, each of the first and second grooves 394 is depicted as semi-circular in shape, allowing each groove 394 to readily and easily receive the corresponding circular sealing mechanisms 282 disposed on each side 133 of the base 132 when the needle assembly 130 is moved back into the retracted position. Alternatively, each groove 392 may take the form of various other shapes and still fall within the scope of the present disclosure. More specifically, and in another example, the shape of each groove 394 essentially matches the shape of each sealing mechanism 282 of the base 132, allowing each groove 392 to easily receive the corresponding sealing mechanism 282, e.g., a frictional element, on each side 133 of the base 132 to secure the base 32 of the needle or cannula assembly 130 in the retracted position and prevent reuse. In operation, pressure is supplied to the first opening 120 of the housing 110 of the insertion mechanism 200 to deploy the needle or cannula 140 of the needle or cannula assembly 130. More specifically, when an amount of pressure P1 in the proximal chamber 118 applies an application force to the proximal surface 134 of the base 132 that exceeds or surpasses the resistive force of the at least one frictional element 280, the needle or cannula assembly 130 is moved from the retracted position to the extended position. In another example, when the amount of pressure P1 in the proximal chamber 118 imparts an application force on the base 132 that exceeds the resistive force applied to the base 132 by the pressure P2 in the distal chamber 119, the needle or cannula assembly 130 is moved from the retracted position to the extended position to deploy the needle.

In this example, the at least one groove 392 increases a force threshold before which the needle assembly 130 will move. The force threshold is much greater than just a frictional resistance, for example. More specifically, and in one example, the force threshold is at least five times greater than the frictional resistance. Said another way, in this example, the resistive force of the at least one frictional element 280 and the at least one groove 392 together is much greater than the resistive force of just the at least one frictional element 280 without any groove 392 (FIG. 5). One of ordinary skill in the art will understand that the force threshold of the frictional element 280 and groove 392 together may be less than or more than five times greater than the frictional resistance and still fall within the scope of the present disclosure, provided the force threshold is still greater than the frictional resistance.

This configuration with the at least one groove 392 allows more build-up of pressure and insures a rapid insertion or deployment of the needle 140. If there is a low force of resistance then the needle assembly 130 may begin to move slowly. A speed of 1 m/s of the needle 140 is desired during needle deployment or insertion. The extra initial resistance in this example allows rapid initial acceleration, even if the pressure does not continue to ramp or increase in the proximal chamber 118 after the needle 140 begins to move.

The pressure P1 may be vented or a negative pressure may be applied to the proximal chamber 118 through the first opening 120 to decrease the pressure P1 in the proximal chamber 118. When the pressure P1 in the proximal chamber 118 is less than the pressure P2 in the distal chamber 119, the needle 140 may move back to the retracted position from the extended position. Said another way, when the pressure P2 exceeds the pressure P1 after deployment of the needle 140, the needle 140 and needle assembly 130 are moved back to the retracted position from the extended position.

After the needle or cannula assembly 130 is moved back into the retracted position, the insertion mechanism 300 also secures the needle or cannula assembly 130 in the retracted position to prevent reuse of the needle 140, for example. More specifically, and as further depicted in FIG. 6, the at least one groove 392 receives the at least one frictional element 282, such as a sealing mechanism, disposed on the sidewall 133 of the base 132 to prevent the needle 140 from being reactivated into the extended position. Said another way, the at least one groove 392 includes the first and second grooves 394, each of which receive the corresponding frictional element 282, such as one or more of the sealing mechanism, an o-ring or a C-clip, disposed on each sidewall 133 of the base 132 to secure the base 132 of the needle or cannula assembly 140 in the retracted position and prevent redeployment of the needle 130. In one example, the high friction between each groove 394 and the frictional element 282 stops movement of the needle assembly 130 after it is moved back to the retracted position and secures the needle assembly 130 in the retracted position.

Figure 7:
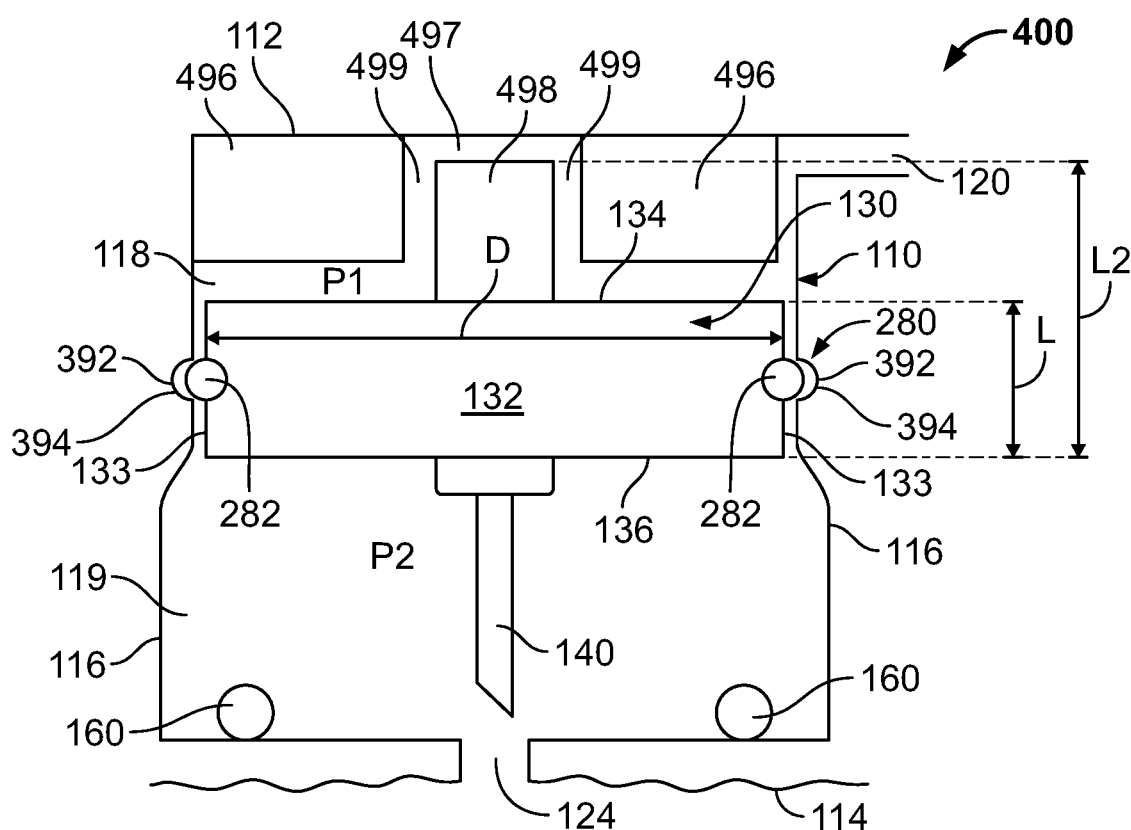
FIG. 7 is a cross-sectional view of another insertion mechanism according to yet another aspect of the present disclosure, the insertion mechanism in a retracted position.

Referring now to FIG. 7, another exemplary insertion mechanism 400 according to the present disclosure is depicted. More specifically, and like the insertion mechanism 300 of FIG. 6, the retraction member of the insertion mechanism 400 is not a spring 142, as depicted in FIG. 2, for example, but instead includes at least one frictional element 280 in contact with the base 132. The at least one frictional element 280 applies a resistive force to maintain the needle or cannula assembly 130 in the retracted position, as explained above. In addition, the insertion mechanism 400 also includes a modified base 132 and a volume of the proximal chamber 118 that is less than the volume of the proximal chambers 118 of the insertion mechanisms 100, 200, and 300 of FIGS. 2, 5, and 6, respectively, as explained more below. More generally, the insertion mechanism 400 is identical to the insertion mechanisms 100 and 300 depicted in FIGS. 2 and 6, respectively, except for the additional and/or alternative structural features included in FIG. 7 and also explained below. For the sake of brevity, parts of the insertion mechanism 400 identical to the insertion mechanism 100 share the same reference numerals and are explained relative to the insertion mechanisms 100 and 300.

More specifically, the insertion mechanism of FIG. 7 further includes a guide member 496 downwardly extending from the proximal end 112 of the housing 110. One side of the guide member 496 is in contact with the sidewall 116 of the housing, while the other side of the guide member 496 is spaced from another area of the sidewall 116 to allow pressure being supplied through the first opening 120 to enter the proximal chamber 118, for example. The guide member 496 includes a central bore 497, and is cylindrical in shape, in one example. One of ordinary skill in the art will appreciate that the guide member 496 may alternatively take the form of various other shapes and still fall within the scope of the present disclosure. In another example, the guide member 496 may include a pair of guide members 496, such that the guide member 496 is not comprised of a single body piece, but instead includes a two part form. In this example, each guide member 496 of the pair of guide members 496 may be one or more of circular, cylindrical, semi-circular, semi-cylindrical or rectangular in shape, for example, or any other shape or combinations of shapes and still fall within the scope of the present disclosure.

In addition, base 132 further includes a guide shaft 498 extending from a center of the proximal surface 134 of the base 132 toward the proximal end 112 of the housing 110. The guide shaft 498 extends into the central bore 497 of the guide member 496. In this way, the central bore 497 of the guide member 496 serves to guide the shaft 498 of the base 132 when the needle assembly 130 moves between the retracted and extended positions. Said another way, the central bore 497 is a guiding bore 497 of the guide member 496 that receives and guides the shaft 498 during deployment and retraction of the needle 140. As further depicted in FIG. 7, there is a small, radial gap 499 on either side of the guide shaft 498 when the guide shaft 498 is disposed within the central bore 497. As further depicted, the diameter of the guide shaft 498 is less than the diameter D of the base 132 of the needle assembly 130.

So configured, the volume of the proximal chamber 118 is less than the proximal chamber 118 of the insertion mechanism 300 of FIG. 6, for example, without sacrificing the stability of the needle assembly 130 while moving from and between the retracted and extended positions. In addition, by including the guide shaft 498 on the base 132, the effective length of base 132 increases from L, as in other insertion mechanisms 100, 200, 300, to a greater length of L2, as depicted in FIG. 7. This increased length increases the stability of the base 132 while keeping the diameter D of the base constant to maintain a desired insertion force per available pressure, for example.

In one example, reducing the diameter D of the base 132 results in less insertion force per available pressure. In addition, decreasing the length L of the base 132 reduces the stability and predictability of the base 132 and, thus, movement of the needle assembly 130 when the guide shaft 498 is not included, for example. Therefore, by including the guide shaft 498 extending from the base 132 toward the proximal end 112 of the housing 110, the effective length of the base 132 and guide shaft 498 together increases to L2, while the diameter D of the base 132 stays the same to maintain the stability of the base 132 and movement of the needle assembly 130.

In view of the foregoing, one of ordinary skill in the art will appreciate the following example method of inserting a needle or cannula 140 of the needle or cannula assembly 130 of any of the insertion mechanisms 100, 200, 300, 400 for the drug delivery device 10 (FIG. 1) into a patient's skin.

More specifically, the method includes maintaining a retracted position of the needle or cannula assembly 130 disposed within the housing 110 of the insertion mechanism 100, 200, 300, 400 by the retraction member. The method also includes supplying pressure to the first opening 120 of the housing 110 of the insertion mechanism 100, 200, 300, 400 until the amount of pressure P1 in a proximal chamber 118 of the housing 110 imparts an application force on the base 132 of the needle or cannula assembly 130 that exceeds a resistive force applied to the base 132 by one or more of the retraction member or a pressure P2 in the distal chamber 119. In addition, the method includes moving the needle assembly 130 from the retracted position to the extended position upon the application force surpassing the resistive force, and disposing the needle 140 of the needle or cannula assembly 130 through a second opening 124 in a distal end 114 of the housing 110 of the insertion mechanism 100, 200, 300, 400 upon movement of the needle assembly 130 to the extended position to deploy the needle 140.

In one example, and as explained above, maintaining the retracted position of the needle or cannula assembly 130 comprises applying a resistive force to the distal surface 136 of the base 132 of the needle assembly 130 via the biasing mechanism 142. In another example, maintaining the retracted position of the needle or cannula assembly 130 comprises disposing a frictional element 282 on a sidewall 133 of the base 132 and applying a resistive force toward the proximal end 112 of the housing 110 via the frictional element 282.

In yet another example, the method may also include one of supplying negative pressure through the first opening 120 or positive pressure to a third opening 284 (FIG. 6) disposed in the housing near the distal end 114 of the housing 110 until a pressure P2 in a distal chamber 119 of the housing 110 exceeds the pressure P1 in the proximal chamber 118. This in turn causes the needle or cannula assembly 130 to move from the extended position to the retracted position.

The method may further include securing the needle assembly 130 in the retracted position after movement from the extended position to prevent redeployment of the needle 140 of the needle assembly 130. In one example, securing the needle assembly 140 in the retracted position comprises providing at least one spring-loaded directional latch 288 on the sidewall 116 of the housing 110 that contacts either side 133 of the base 132 upon movement into the at least one spring-loaded directional latches 288. In another example, securing the needle assembly 130 in the retracted position to prevent redeployment includes inserting at least one sealing mechanism 282 disposed on each side 133 of the base 132 into a corresponding groove 392 disposed on the sidewall 116 of the housing 110. In any case, the method may also comprise increasing a size of the proximal chamber 118 as the needle or cannula assembly 130 moves from the retracted position to the extended position and reducing an output force present at a time of needle deployment.

One of ordinary skill in the art will appreciate many of the advantages of the foregoing insertion mechanisms 100, 200 and 300 and methods of the present disclosure. For example, in each of the insertion mechanisms 100, 200, 300, the insertion force and speed of the needle or cannula 140 of the needle or cannula assembly 130 can be controlled by adjusted the pressure supplied by the pressure supply device 126, for example, or any other pressure source, the flow rate, and/or the proximal surface 134 of the base 132 that receives the applied pressure P1 in the proximal chamber 118, for example. In addition, by including the o-rings or similar sealing mechanisms in the distal chamber 119 just before the distal end 114 of the housing 110, allows the distal surface 136 of the base 132 to slightly "bounce" upon contact with the o-rings 160 when moved to the extended position. This slight "bounce" creates a slight over-penetration of the needle 140 during initial insertion, which may reduce the incidence of tissue blocking the needle or cannula 140.

Further, a preferred insertion speed may require a build-up of pressure P1 in the proximal chamber 118 before release of the needle or cannula assembly 130 with a drop-off in frictional forces just prior to skin entry in the patient. As a result, a sufficient force is present for insertion, making insertion quicker and less painful. The insertion mechanisms 100, 200, 300, 400 may also increase patient comfort and decrease potential patient anxiety. For example, in conventional methods and mechanisms, patients may be required to insert the rigid needle into themselves as they advance a button into the device. This type of insertion mechanism may be a cause of anxiety or intimidation to the patient because they are controlling the insertion of the trocar with the advancement of the button. Additionally, known methods and mechanisms include rigid needles combined with an external safety guard that may remain in the patient's skin when the patient is removing the wearable device. In contrast, the disclosed wearable drug delivery device may have a smaller injection site and can be configured to retract the cannula 140 before the patient removes the wearable device. In addition, the automatic deployment and retraction of the needle 140 keeps the needle 140 always hidden and provides better comfort to the patient when the wearable drug delivery device is removed. Further, retraction of the needle 140 can also help the patient understand that the injection is finished, or, if there is an error, that it is acceptable to remove the wearable drug delivery device once the needle 140 has been retracted. However, the scope of the present disclosure is not limited to these or any other benefits and advantages described herein, and other benefits and advantages may result from the disclosed embodiments and any modifications thereto in accordance with principles of the present disclosure.

The above description describes various systems and methods for use with a drug delivery device. It should be clear that the system, drug delivery device or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof: OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C1K; 2×L1C; Con4C; Con4C1K; 2×Con4C1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003)

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/

0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (y4), deposited at the ATCC under number PTA-5214, and a light chain encoded by a polynucleotide in plasmid 15H12/19D12 LCF (K), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MY0-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRa antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Varghehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BITE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug injection device, systems, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the devices, systems, methods, and their elements.

What is claimed is:

1. A wearable drug delivery device comprising:
   a main housing having a container, a fluid pathway connector coupled to the container, and a pressure supply device; and
   an insertion mechanism disposed within the main housing and operatively coupled to the pressure supply device, the fluid pathway connector defining a fluid flow path between the container and the insertion mechanism, the insertion mechanism including:
     a housing having a proximal end, a distal end, a sidewall disposed between the proximal and distal ends, a first opening disposed near the proximal end, and a second opening disposed in the distal end, the first opening coupled to the pressure supply device,
     a needle or cannula assembly disposed within the housing and moveable between a retracted position and an extended position, the needle or cannula assembly including a base having a proximal surface and a distal surface, and a needle or a cannula coupled to the distal surface of the base and disposed between inside surfaces of the sidewall of the housing, the base dividing the housing into a proximal chamber and a distal chamber, and
     a retraction member disposed within the housing to maintain the needle or cannula assembly in the retracted position before movement to the extended position, the retraction member in contact with the base and applying a resistive force,
   wherein the pressure supply device supplies pressure through the first opening and into the proximal chamber until an amount of pressure P1 in the proximal chamber applies an application force to the proximal surface of the base of the needle or cannula assembly that surpasses the resistive force of the retraction member to move the needle or cannula assembly from the retracted position to the extended position, the needle or the cannula disposed through the second opening in the distal end of the housing in the extended position to deploy the needle or the cannula, and
   wherein the needle or cannula assembly is secured back into the retracted position after movement from the extended position by one or more of: (1) at least one spring-loaded directional latch disposed on the sidewall of the housing, with the needle or cannula disposed between the inside surfaces of the sidewall, or (2) at least one groove disposed on the sidewall of the housing, the at least one groove for receiving at least one sealing mechanism disposed on a sidewall of the base.

2. The wearable drug delivery device of claim 1, wherein the retraction member comprises a biasing mechanism, the biasing mechanism including one or more of: a spring having a first end attached to the base and a second end attached to the distal end of the housing, or a flexible fluid path member having a first end attached to the base and a second end attached to the proximal end of the housing, and wherein the biasing mechanism retracts the needle or the cannula into the retracted position after release of the pressure P1 in the proximal chamber.

3. The wearable drug delivery device of claim 2, wherein the insertion mechanism further comprises a first connector upwardly extending from the proximal surface of the base, and the flexible fluid path member having the first end of the flexible fluid path member operatively coupled to the first connector upwardly extending from the proximal surface of the base and the second end of the flexible fluid path member operatively coupled to a second connector downwardly extending from the proximal end of the housing, the flexible fluid path member moveable with the needle or cannula assembly.

4. The wearable drug delivery device of claim 2, further comprising a step disposed on the sidewall of the housing near the distal end of the housing, the step having a sealing mechanism, wherein the sealing mechanism is an o-ring, and the distal surface of the base contacts the o-ring to soften an impact when the needle or cannula assembly moves from the retracted position to the extended position.

5. The wearable drug delivery device of claim 2, wherein the housing includes the sidewall having a threaded inside surface, and the base further includes a side surface in contact with the threaded inside surface of the sidewall, the side surface of the base having a threaded surface corresponding to the threaded inside surface of the sidewall of the housing.

6. The wearable drug delivery device of claim 1, wherein the retraction member comprises at least one frictional element, the at least one frictional element in contact with the sidewall of the base and comprising one or more of at least one sealing mechanism or an o-ring.

7. The wearable drug delivery device of claim 6, wherein, upon one of applying negative pressure through the first opening or supplying positive pressure to a third opening disposed in the sidewall of the housing near the distal end of the housing, a pressure P2 in the distal chamber surpasses the pressure P1 in the proximal chamber causing the needle or cannula assembly to move back into the retracted position after the deployment of the needle or the cannula.

8. The wearable drug delivery device of claim 6, wherein the at least one groove for receiving the at least one sealing mechanism disposed on the sidewall of the base prevents the needle or cannula assembly from being activated again into the extended position.

9. The wearable drug delivery device of claim 1, wherein the at least one spring-loaded directional latch includes a first spring-loaded directional latch disposed on one area of the sidewall of the housing and a second spring-loaded latch disposed on another area of the sidewall of the housing, each of the first spring-loaded directional latch and the second spring-loaded latch having an angled side surface that contacts a corresponding angled side surface of the base on either side of the base to lock the base of the needle or cannula assembly, preventing redeployment.

10. The wearable drug delivery device of claim 8, wherein the at least one groove includes a first groove disposed on one area of the sidewall of the housing and a second groove disposed on another area of the sidewall of the housing, each of the first groove and the second groove adapted to receive a corresponding frictional element to secure the base of the needle or cannula assembly, preventing redeployment.

11. The wearable drug delivery device of claim 6, wherein the housing further includes a guide member downwardly extending from the proximal end of the housing and having a central bore, and the base further includes a shaft extending from a center of the proximal surface of the base into the central bore, the central bore to guide the shaft of the base when the needle or cannula assembly moves between the retracted position and the extended position and reduce a volume of the proximal chamber.

12. An insertion mechanism for a drug delivery device, the insertion mechanism comprising:
a housing having a proximal end, a distal end, a sidewall disposed between the proximal and distal ends, a first opening disposed in the housing near the proximal end, the first opening adapted to be operatively coupled to a pressure supply device, and a second opening disposed in the distal end of the housing;
a needle or cannula assembly disposed within the housing and moveable between a retracted position and an extended position, the needle or cannula assembly including a base having a proximal surface and a distal surface, and a needle or a cannula attached to the base and disposed between inside surfaces of the sidewall of the housing;
a retraction member in contact with the base and applying a resistive force to maintain the needle or cannula assembly in the retracted position before movement to the extended position; and
a flexible fluid path member having a first end operatively coupled to a connector extending from the proximal surface of the base and a second end operatively coupled to a connector extending from the proximal end of the housing,
wherein, pressure is supplied through the first opening until an amount of pressure P1 applies an application force to the proximal surface of the base of the needle or cannula assembly that exceeds the resistive force of the retraction member to move the needle or cannula assembly from the retracted position to the extended position, the needle or the cannula extending through the second opening in the distal end of the housing in the extended position.

13. The insertion mechanism of claim 12, wherein the base divides the housing into a proximal chamber and a distal chamber, such that when the pressure P1 in the proximal chamber exceeds a pressure P2 in the distal chamber, the needle or cannula assembly moves from the retracted position to the extended position.

14. The insertion mechanism of claim 12, further comprising a pair of sealing mechanisms disposed on the sidewall of the housing near the distal end of the housing, such that the distal surface of the base contacts the pair of sealing mechanisms when the needle or cannula assembly is in the extended position.

15. The insertion mechanism of claim 12, wherein the housing includes the sidewall having a threaded inside surface, and the base further includes a side surface in contact with the threaded inside surface of the sidewall, the side surface of the base having a threaded surface corresponding to the threaded inside surface of the sidewall of the housing, and wherein the threaded inside surface of the sidewall of the housing and the threaded surface of the side surface of the base are one of coarse threading or fine threading, the coarse threading allowing the needle or the cannula to rotate at least two to three times during insertion, and the fine threading allowing the needle or the cannula to rotate at least eight to ten times during insertion.

16. The insertion mechanism of claim 12, wherein the flexible fluid path member is moveable between a retracted position and an extended position corresponding to the retracted position and the extended position of the needle or cannula assembly.

17. A method of deploying a needle or a cannula of an insertion mechanism from a drug delivery device, the method comprising:
   maintaining a retracted position of a needle or cannula assembly disposed within a housing of the insertion mechanism by a retraction member, the housing including a sidewall and the needle or cannula assembly including the needle or the cannula disposed within the housing between inside surfaces of the sidewall;
   supplying pressure to a first opening in a proximal end of the housing of the insertion mechanism until an amount of pressure P1 in a proximal chamber of the housing imparts an application force on a base of the needle or cannula assembly that exceeds a resistive force applied to the base by one or more of the retraction member or a pressure P2 in a distal chamber of the housing;
   moving the needle or cannula assembly from the retracted position to an extended position upon the application force surpassing the resistive force;
   disposing the needle or the cannula of the needle or cannula assembly through a second opening in a distal end of the housing of the insertion mechanism upon movement of the needle or cannula assembly to the extended position to deploy the needle or the cannula; and
   securing the needle or cannula assembly in the retracted position after movement from the extended position, wherein securing the needle or cannula assembly in the retracted position comprises one of: (1) providing at least one spring-loaded directional latch on the sidewall of the housing that contacts at least one side of the base upon movement into the at least one spring-loaded directional latch, or (2) inserting at least one sealing mechanism disposed on the at least one side of the base into a corresponding groove disposed on the sidewall of the housing.

18. The method of claim 17, wherein maintaining the retracted position of the needle or cannula assembly comprises one of: (1) applying the resistive force to a distal surface of the base of the needle or cannula assembly via a biasing mechanism, or (2) disposing a frictional element on a sidewall of the base and applying the resistive force toward the proximal end of the housing via the frictional element.

19. The method of claim 17, further comprising at least one of:
   (a) supplying negative pressure through the first opening until the pressure P2 in the distal chamber of the housing exceeds the pressure P1 in the proximal chamber thereby causing the needle or cannula assembly to move from the extended position back to the retracted position; or
   (b) supplying positive pressure to a third opening disposed in the housing near the distal end of the housing until the pressure P2 in the distal chamber of the housing exceeds the pressure P1 in the proximal chamber, thereby causing the needle or cannula assembly to move from the extended position back to the retracted position.

* * * * *